United States Patent [19]
Freeman et al.

[11] Patent Number: 5,088,484
[45] Date of Patent: Feb. 18, 1992

[54] ORTHOPEDIC CASTING BANDAGE

[75] Inventors: Horace L. Freeman, Burlington, N.C.; Hee K. Yoon, North Brunswick, N.J.

[73] Assignee: Carolina Narrow Fabric Company, Winston-Salem, N.C.

[21] Appl. No.: 593,852

[22] Filed: Oct. 5, 1990

[51] Int. Cl.$^5$ .................. A61L 15/00; A61F 5/04
[52] U.S. Cl. .................... 602/44; 602/900; 602/8
[58] Field of Search ............ 128/89 R, 89 A, 90, 128/91 R, 165, 166, 155–156; 428/255, 273, 542.8, 913

[56] References Cited

U.S. PATENT DOCUMENTS

| | | | |
|---|---|---|---|
| 2,905,174 | 5/1959 | Smith | 128/156 |
| 3,447,887 | 6/1969 | Lindenhovius et al. | 8/930 |
| 3,589,934 | 6/1971 | Schimmel | 8/553 |
| 3,970,422 | 7/1976 | Maeda et al. | 8/553 |
| 4,045,601 | 8/1977 | Brodmann et al. | 8/523 |
| 4,161,176 | 7/1979 | Harris, II et al. | 128/155 |
| 4,256,459 | 3/1981 | Russell et al. | 8/930 |
| 4,306,549 | 12/1981 | Canie | 128/90 |
| 4,376,438 | 3/1983 | Straube et al. | 128/90 |
| 4,406,662 | 9/1983 | Beran et al. | 8/471 |
| 4,433,680 | 2/1984 | Yoon | 128/90 |
| 4,452,607 | 6/1984 | Wessely | 8/930 |
| 4,455,147 | 6/1984 | Lewis et al. | 8/930 |
| 4,574,793 | 3/1986 | Lee | 128/90 |
| 4,745,912 | 5/1988 | McMurray | 128/90 |
| 4,781,725 | 11/1988 | Dunn, Jr. et al. | 8/930 |
| 4,800,872 | 1/1989 | Buese | 128/90 |
| 4,934,356 | 6/1990 | Klintworth | 428/255 |
| 4,940,047 | 7/1990 | Richter | 128/90 |
| 4,946,726 | 8/1990 | Sandvig | 128/90 |
| 4,984,566 | 1/1991 | Sekine | 128/90 |

FOREIGN PATENT DOCUMENTS

WO90/14060 11/1990 PCT Int'l Appl.

Primary Examiner—Robert A. Hafer
Assistant Examiner—Michael Brown
Attorney, Agent, or Firm—Bell, Seltzer, Park & Gibson

[57] ABSTRACT

The invention provides improved orthopedic cast bandages and improved orthopedic casts which include one or more colors. The orthopedic cast bandages of the invention comprise an open mesh fabric tape and a hardenable liquid resin coated onto the fibrous tape. At least one coloring agent is visibly disposed on at least a portion of the fibrous tape. The coloring agent is stably retained by the fibrous tape in the presence of the hardenable liquid resin. Because the coloring agent is stably retained by the fibrous tape, the invention provides for colored orthopedic casting tapes which do not require the use of colored liquid resins. In addition, multiple colored, patterned orthopedic casts, not heretofore available, are provided by the invention.

33 Claims, 2 Drawing Sheets

ORTHOPEDIC CASTING BANDAGE

FIELD OF THE INVENTION

The invention relates to an improved orthopedic casting bandage and to orthopedic casts. More specifically, the invention relates to improved orthopedic casting bandages capable of forming single and multi-colored casts.

BACKGROUND OF THE INVENTION

Polymeric casting materials have gained widespread commercial acceptance during the past decade. As compared to Plaster of Paris casts, the polymeric or so-called "synthetic" casting materials have advantages of being light weight, and strong. Synthetic casting materials are also porous in the hardened state so that the cast is breathable. Typically, orthopedic synthetic casts are made from a curable resin-impregnated narrow fabric or casting tape. The fabric, which is preferably knit, can be formed of glass fibers and/or synthetic fibers such as polyester, nylon, polyolefins and the like.

Polyurethane casting materials which have experienced widespread commercial acceptance are disclosed in Yoon U.S. Pat. 4,433,680. These casting materials employ a water activatable polyurethane prepolymer which contains a dimorpholinodiethylether catalyst. The compositions have a long shelf life during which the polyurethane polymer remains in the liquid state. When the bandage is to be used, it is removed from a sealed package and placed in water for a few seconds. It is removed from the water and applied to the patient usually over a tubular, knitted fabric and a padding. The bandage will set rapidly to a condition where it is capable of immobilizing a fracture.

More recently, colored casting materials have gained widespread commercial acceptance. Coloring of casting materials has been accomplished by adding pigments or dyes to the prepolymer materials as disclosed, for example, in Straube et al. U.S. Pat. No. 4,376,438 and in Klintworth, Jr. U.S. Pat. No. 4,934,356. The pigment and/or dyeing materials added to the prepolymer materials are chosen carefully to avoid causing the prepolymer to gel and/or harden prematurely.

In practice, the colored orthopedic casts are highly desirable to many patients. There are, however, a number of disadvantages associated with the colored casts. In the medical cast room, the colored prepolymers while in the liquid state, can stain tables, floors and other surfaces, causing an undesirable casting room appearance and atmosphere. Similarly, clothing and lab coats of physicians and cast technicians are stained by contact with the colored polymer. In the manufacturing operation, changing from one color prepolymer to another can require cleaning of the coating machinery including removal and cleaning of coating rolls, and flushing of the interior of the coating apparatus.

As colored casting materials have increased in popularity, substantial interest has been expressed for multiple colored and patterned casts. Spirally striped casts have been made by the concurrent winding of two differently colored, separate casting tapes around the fractured limb of the patient. Patterned casts have also been made by forming the main cast body out of a single colored casting material followed by attachment to the surface of the cast, of separate casting materials of different colors which have been precut into desired shapes. A multiple-colored, patterned sleeve for wearing over a cast has also been sold commercially.

Despite the apparent interest in multicolored casts, no practical multicolored casting material has been proposed or previously made available. Physicians and cast technicians have thus only been able to provide multicolored casts by employing several, different colored separate casting bandages in the construction of the cast. In view of the demands on the time and skill of the medical personnel, multicolored casting materials are thus not practically available.

SUMMARY OF THE INVENTION

This invention provides orthopedic casting materials which provide single colored and/or multiple colored, patterned orthopedic casts without requiring the use of colored polymers to form a single colored cast or multiple, separately colored casting bandages to form a multiple colored cast. The casting bandages of the invention can be applied to the patient in the conventional and normal manner. The cast bandage of the invention comprises an open mesh fibrous tape together with a hardenable liquid resin coated on the fibrous tape and which is capable of curing to form a substantially translucent or transparent hardened plastic. At least one coloring agent is stably retained by the fibrous tape in the presence of the hardenable liquid resin and is visibly disposed on at least a portion of the fibrous tape. Advantageously, at least two different coloring agents are visibly disposed on a portion or all of the fibrous tape and form a predetermined, visible pattern of at least two colors.

In one preferred embodiment of the invention, the coloring agent or agents disposed on the fibrous tape comprise one or more dyes which have been penetrated into or chemically bound to fibers of the fibrous tape. The fibrous tape is advantageously composed of one or more natural or synthetic fibers conventionally used to form a plastic orthopedic cast. The fibers can include cotton, nylon, polyester, acrylic, glass fibers and the like. Advantageously, the coloring agent disposed on or in the fibers of the fibrous tape is stably retained by the fibers in the presence of the hardenable liquid resin for substantial periods of time, for example, from several months to in excess of a year, without any adverse effect by the liquid resin on the coloring agent and without any adverse effect by the coloring agent on the liquid resin.

In one greatly preferred embodiment, the coloring agent is applied to the fibrous substrate by a transfer printing process which involves a heat driven sublimation dyeing of the fibrous tape. When the fibrous substrate is a synthetic material, preferably polyester, the tape can be made in a multitude of one or more deep, rich clearly defined colors even though the fibrous tape is a porous, open mesh material. Transfer printed patterns on the fibrous tape are crisp and of high resolution without substantial bleeding of one portion of the pattern onto or into other portions of the pattern. Advantageously the open mesh fibrous tape has an extensibly of greater than about fifteen percent prior to the hardening of the liquid resin.

The orthopedic cast bandaging material of the invention can be used for all layers of an orthopedic cast or can be used only as the outer, visible layers of the orthopedic cast. In either case, the visible colored portion or portions of the orthopedic cast are stably retained within the hardened polymer. Because there is no requirement that the hardenable resin, itself, be colored, the orthopedic bandages of the invention can be used without color staining of medical facilities and/or clothing of physicians and patients. Casting bandages of different colors, designs and patterns can be precoated using the same coating equipment without the necessity of rinsing and cleaning to remove colored prepolymers between manufacturing runs. The invention provides patterned casting materials in a variety of designs which can be attractive and desirable to children, adolescents and adults and can aid in lessening the mental trauma associated with repair of a fractured bone and/or can minimize the stigma associated with long term cast confinement.

BRIEF DESCRIPTION OF THE DRAWINGS

In the drawings which form a portion of the original disclosure of the invention.

DETAILED DESCRIPTION OF THE PREFERRED EMBODIMENTS

Figure 1:
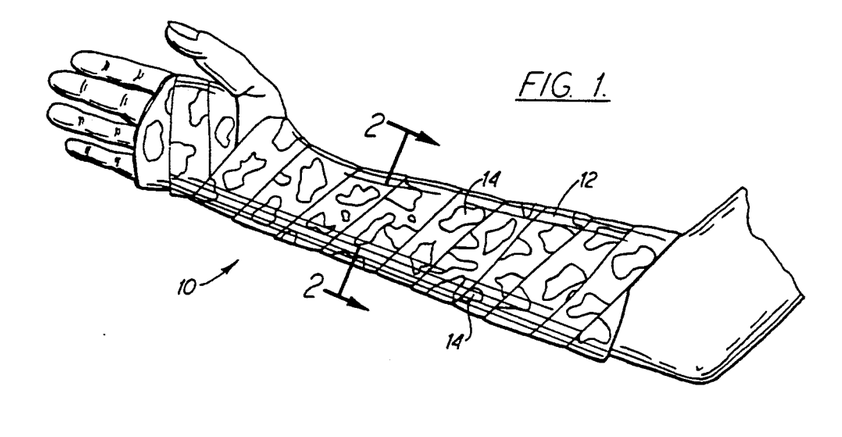
FIG. 1 illustrates a patterned orthopedic ion about the forearm of a patient.

FIG. 1 illustrates a patterned cast 10 according to the invention. The cast 10 includes a continuous patterned casting tape 12 disposed on the outer layer of the cast. Casting tape 12 includes patterned areas 14 which are provided by one or more coloring agents visibly disposed on the fibrous tape 12. As illustrated, the visibly disposed coloring agents, taken together, form a camouflage-type pattern which would be considered desirable by a child or adolescent.

Figure 2:
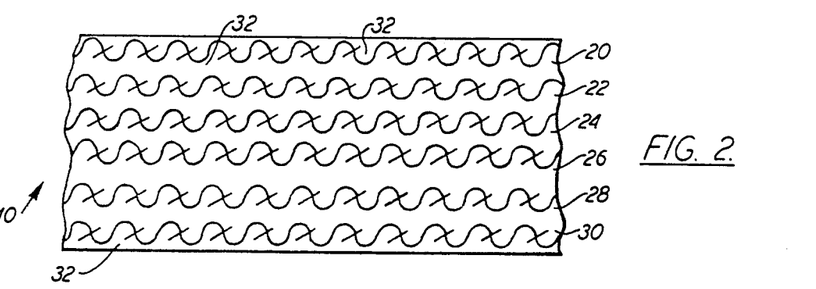
FIG. 2 illustrates a greatly enlarged, partial cross-sectional view of the cast of FIG. 1 taken along line 2—2.

As illustrated in FIG. 2, the cast of FIG. 1 is typically composed of a plurality of layers 20, 22, 24, 26, 28 and 30. It will be apparent to the skilled artisan that although six layers are illustrated in FIG. 2, a typical orthopedic cast can be composed of greater or fewer numbers of layers depending upon the requirements. At least the exterior layer 20 of the cast 10 includes the coloring agent 14, (FIG. 1) visibly disposed on the surface thereof. The remaining layers of the casting tape, 22-30 can be the same or different fibrous casting tape as used for layer 20. Thus, for example layer 20 can be a polyester fibrous tape coated with a hardened, translucent or transparent plastic while layers 22-30 can be composed of glass fibers and/or glass fibers in combination with elastomeric fibers as disclosed in for example, Buese U.S. Pat. No. 4,668,563 which is hereby incorporated by reference. Interior layers 22-30 can be provided with or without a color patterned surface.

Intimately surrounding each of layers 20-30 is a hardened polymer matrix material 32. Although not shown in FIG. 2, because fibers layers 20-30 are porous and open mesh, the resultant cast 10 is likewise porous and breathable; thus, there are numerous openings in the hardened polymer matrix 32 throughout the hardened cast 10.

Figure 3:
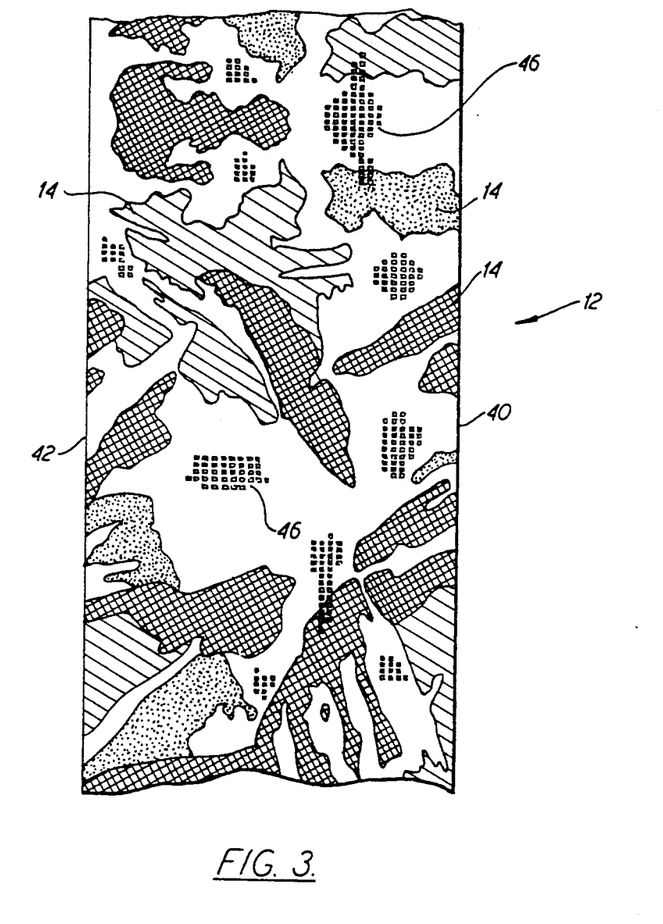
FIG. 3 illustrates a porous, open mesh fibrous casting tape having coloring agents stably retained by the fibers thereof and exhibiting a crisp pattern of high resolution.

FIG. 3 illustrates a patterned casting fabric advantageously employed in the orthopedic casting tapes of the invention. As illustrated, fabric 30 is a knit, open mesh fabric including selvage edges 40 and 42 on the opposed transverse edges thereof. The open mesh fibrous tape 12 includes numerous pores 46 throughout the structure of the fabric which allow full and complete penetration of the hardenable liquid polymer into the fabric and provide porosity in the hardened cast. The fabric 12 includes a plurality of predetermined colored portions 14, of different colors visibly disposed on the surface of the fabric. Even though the fabric is porous and open mesh, the patterns are seen to be crisp and of high resolution. In practice, casting tapes are typically available in widths ranging from about two inches (5 centimeters) to about 5 inches (about 13 centimeters).

Patterned areas 14 are applied to the casting tape 12 prior to application of the liquid polymer. The patterned areas can be prepared by stably disposing a coloring agent on at least one side of the fabric by various known processes including pigment printing, wet printing and transfer printing. As known to the skilled artisan, pigment printing involves use of inks made of pigment, resin and solvent. The ink is applied to the fabric and the fabric is then passed through a curing oven. The heat evaporates the solvent and fuses the resin and the pigment onto the fabric. The colors do not penetrate inside the fiber, but stay on the surface of it, like a paint. Wet printing employs dyes which penetrate into or combine chemically with the fiber. Wet printing can involve various operations following the dye application step to develop the dyes, wash off the chemicals, and restore the fabric to an acceptable form. As discussed in greater detail later, the colored areas 14 on casting tape 12 are preferably applied by the process of transfer printing in which a sublimable dye is heated to convert the dye into a gas and the gaseous dye then penetrates into or combines chemically with the fiber surface.

Figure 4:
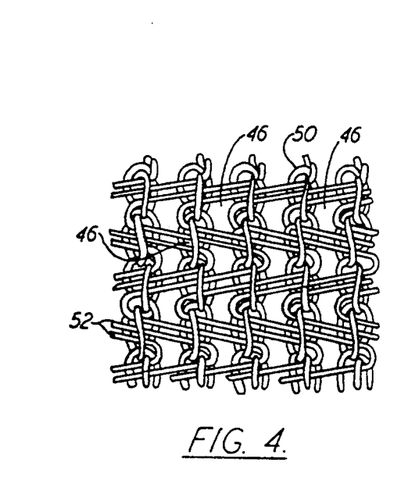
FIG. 4 illustrates one preferred knitting pattern for the open mesh fabric of FIG. 3.

As illustrated in FIG. 4, the fibrous tape for the orthopedic cast is preferably a relatively open and air permeable knitted fabric. The knit patterned shown in FIG. 4 is a Rachell Knit including chain stitches or whales 50 and courses 52. As illustrated in FIG. 4, the courses are in pairs, which results from the particular Rachell Knitting design. The knit structure illustrated in FIG. 4 having paired courses is known as a "two-ply fil". In order to provide distinct and highly visible colors and patterns, it is advantageous to employ two-ply or multi-ply fil knit patterns in fabrics used in the invention. As will also be apparent from FIG. 4, the knit casting tape includes a plurality of open areas 46 which can be in the same plane as the general plane of the fabric or can be in different planes depending upon the construction of the fabric.

Advantageously, the yarns employed to make fabrics such as illustrated in FIG. 4 can be spun yarns, multiple filament flat yarns and/or multiple filament textured yarns. Multiple filament textured polyester yarns and spun polyester yarns provide a desirably optically dense printing surface for the retention of coloring agents. In one particularly preferred embodiment of the invention, the fabric as illustrated in FIG. 4 can be formed using a textured polyester yarn to provide chain stitch 50 and spun polyester yarn to provide courses 52. As discussed in greater detail later, this and similar fabrics can be knit, followed by a heat treatment to shrink the fabric in order to provide an extensibility of greater than about 15% in the longitudinal direction.

Extensibility in the longitudinal direction provides a desirably conformable casting tape which can readily conform to the bandaging surfaces of a patient's limb without requiring the need for so-called "tucks", wherein a portion of the fabric is tucked underneath itself. Whether or not the fabric is extensible; and whether or not the fabric is shrunk, advantageously the fabric, as printed, has an optical density, as determined by the number of whales, courses, weave pattern and fabric construction, so that the coloring agent can readily be applied to the fabric. Fabrics having about 8-15 whales per inch and between about 12 and about 20 courses per inch (in a two-ply fil fabric) have been found particularly advantageous.

Figure 5:
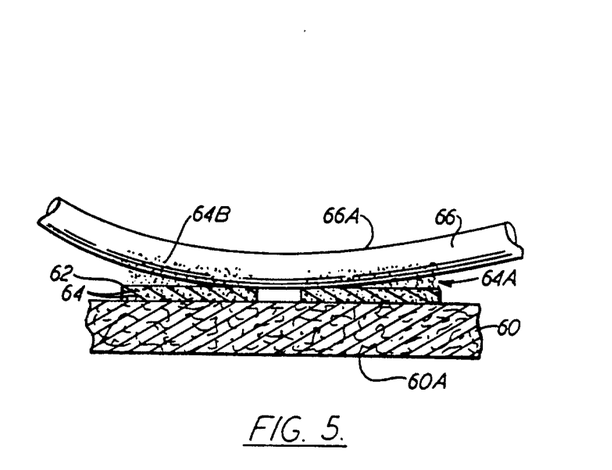
FIG. 5 illustrates operation of transfer printing which is used to provide dyed patterns on fibrous substrates in preferred embodiments of the invention.

FIG. 5, illustrates operation of the preferred transfer printing process which is advantageously employed to stably color casting tapes of the invention. Transfer printing is a two-step process. First, the desired color or pattern is printed on paper substrate 60 using a resin based ink 62 containing a sublimable dye indicated generally by dots 64. Next, the printed paper is placed in contact with a fabric represented by fiber 66. Heat and pressure are applied to the back 60a of paper substrate 60. The dye which is bound within the resin ink 62 is converted into a gas 64a by the heat and the dye condenses on the fiber surface and subsequently diffuses into the interior of the fiber. As shown in FIG. 5, the dye 64b in the fiber surface typically diffuses only partially through the fiber with the result that the backside 66a of transfer printed fabrics are usually not colored.

The transfer printing process is known in the art and is discussed in detail in various publications available to the skilled artisan. Specific information regarding transfer printing can be found, for example, in PROCEEDINGS, SYMPOSIUM ON TRANSFER PRINTING; The 46th TRIANNUAL RESEARCH AND TECHNOLOGY CONFERENCE (Mar. 24-25, 1976) published by Textile Research Institute, Princeton, New Jersey; and in TRANSFER PRINTING MANUAL, Charles Reichman, Ed.; National Knitted Outerwear Association, New York, N.Y. (1976). The foregoing materials are hereby incorporated by reference.

Transfer printing (also known as heat transfer printing or sublimation printing) is typically accomplished using disperse dyes and a heating temperature of on the order of 200° C., for example 210° C. Sublimable disperse dyes are well known to the skilled artisan and are discussed in greater detail in the above-identified references. Heat transfer printing is particularly effective on polyester fabrics but can also be used on natural fibers, nylon and acrylic fibers. For example, with nylons it is possible to introduce into to the structure of a conventional disperse dye, a reactive moiety capable of reacting with the amino group on the polyamide (nylon) substrate. With acrylics, various materials can be added to the printing ink or paste to improve transfer of the dyes. Likewise, with natural materials such as wool and cotton, various pretreatments can be conducted to provide a coating on the fiber surface to make the fibers more receptive to transfer printing. Transfer printing has also been carried out in accordance with this invention, on glass fabrics, i.e., knit casting tapes composed of glass fibers. It has also been found that improved printing on glass fabrics can be accomplished by precoating the glass fabric with a water based acrylic solution followed by a curing treatment at elevated temperatures. Advantageously, the fabric is padded with the resin solution and passed under a radiant heater set to a temperature of greater than 450° C., for example, from 450° to about 600° C., for a time period of from one to about ten minutes, for example, from about two about five minutes. Such treatment can cure the applied resin to provide a glass fabric with a soft hand, but which is coated with a cured acrylic resin. The resultant fiber is thereby provided with a surface coating which is susceptible to absorption or reaction with heat transfer dyes.

It has been found that the transfer printing process is particularly advantageous for providing the casting materials of this invention for a number of reasons. Resins used to impregnate casting materials, and particularly the polyurethane prepolymers, are highly reactive. Thus, in the presence of even minor amounts of moisture the resins are known to gel and/or harden prematurely. Other organic and inorganic chemicals even in minute amounts can cause the premature hardening of the resins. Similarly, the liquid resins are, in many cases good solvents for many organic materials. Thus, various colorant materials can be dissolved by the liquid resins with the result that the resin itself becomes colored and/or the coloring on the fabric bleeds or fades. However, with transfer dyes used in the invention, and particularly with receptive substrates, it has been found that the dye is held fast by the fiber, in many cases for extended periods of time. Moreover, the transfer dyeing process is capable of providing printed patterns on open mesh, highly porous casting tapes while providing a deep, crisp high resolution pattern on the casting substrate.

Preferred casting tapes of the invention are shelf stable when packaged in a sealed pouch with the liquid resin precoated onto the substrate. Advantageously, the resin coated casting materials have a shelf stability as measured by accelerated testing, of at least one week when stored at 50° C. Most advantageously, the casting materials have a shelf stability of greater than about two months when stored at a temperature of 50° C. which is believed to be indicative of a shelf life of about two years or greater under normal conditions. Transfer dyed polyester casting tapes when coated with polyurethane resin compositions as disclosed in Yoon U.S. Pat. No. 4,433,680, which is hereby incorporated by reference, are capable of meeting these shelf stability conditions.

Preferred polyester casting tapes of the invention have an extensibility of greater than about 10%. These polyester casting materials are made by a process wherein the fabric is knit employing a textured polyester yarn as the knit stitch or whale yarns of the knit fabric. Thereafter, the knit yarn is passed through a heated oven or other heating zone in a substantially tensionless condition or under conditions wherein the knit fabric is overfed through the heating zone. For example, the knit fabric can be fed through a heating oven, heated to a temperature of about 400 to 450° F., for example, 425° F., for a period of 10-30 seconds, for example, 20 seconds. During this treatment, the fabric shrinks, for example, in an amount of about 10% to about 30%, to provide a knit polyester fabric having an extensibility of greater than about 15%, preferably greater than about 20%. Extensibility can be measured by attaching a static weight of about 680 grams per inch width of fabric, to the fabric and measuring the resulting fabric extension which is then expressed as a percentage of the fabric length prior to extension.

Following heat treatment to provide extensibility, the fabric is subjected to transfer printing using a continuous drum type transfer printing apparatus as known to the skilled artisan According to another aspect of the invention, it has been found that extensibility in the knit fabric can be maintained following the transfer printing process by feeding the polyester fabric through the transfer printing machine in a relaxed, i.e., tension-free form. This can be accomplished by festooning the unprinted casting tape into containers prior to the transfer printing treatment so that the fabric is not stretched as it is removed from the container and passed through the heated printing zone. The transfer printing step is advantageously conducted at a temperature which is about the same or less than the temperature previously used to shrink the fabric. The casting tape is thereafter advantageously packaged in moisture proof containers, such as plastic bags, following transfer printing so that it does not absorb moisture.

Thereupon, the transfer printed casting tape is treated to apply a polyurethane prepolymer. The prepolymer is applied in a dry atmosphere to the fabric by a reverse roll coating or other coating technique known to form cast bandages. The weight of prepolymer on the fabric can range from about 60 to 400 grams per square meter, preferably between about 80 to 300 grams per square meter to thereby provide a prepolymer weight of between about 30% and 70% by weight, based on the weight of the coated tape. The skilled artisan will recognize that the amount of prepolymer will depend in part on the nature and composition of the fibrous tape and on the specific tape construction. Immediately after the prepolymer is applied to the fabric, the coated fabric is packaged in an inert atmosphere to prevent any contact with atmospheric moisture.

As indicated previously, numerous polyurethane prepolymer are known and can be successfully employed in the invention. The preferred polyurethane prepolymer is made from diphenylmethanediisocyanate containing carbodiimide groups. These diisocyanates are reacted with a polyol containing a plurality of functional groups, for example two to three functional groups. The polyols may be diols or triols or mixtures of diols and triols. Preferred polyols are poly(oxypropylene)glycol having a hydroxyl number of 105 and a poly(oxypropylene)triol having a hydroxyl number of 232. The molecular weight of the polyols is usually below 2,000, preferably in the range of 700 to 1,500, and most preferably between about 700 to 1,000.

The ratio of polyisocyanate to the polyol in the prepolymer reaction mixture is best expressed by the equivalent ratio. Equivalent weight is determined by dividing the molecular weight of each particular component by its functionality or number of functional groups in the compound. The equivalent ratio is the ratio of the equivalency of the isocyanate to the polyol. The equivalent ratio in the preferred systems should be between 2:1 to approximately 15:1 equivalents of the polyisocyanate to the polyol and preferably from 2:1 to 10:1. These components are combined so that there is in excess of from 5% to 30% NCO groups in the prepolymer. The prepolymer also contains from 0.1% to 10% by weight, based on the weight of the total mixture, of the dimorpholinodiethylether catalyst described in the above-identified Yoon patent. Particularly preferred polyurethane prepolymers are described in the working examples of Yoon U.S. Pat. No. 4,433,680.

Various known additives can be incorporated into the prepolymer such as, for example, viscosity modifiers, uv stabilizers and/or antioxidants. Where desirable, various dyestuffs can also be incorporated into the prepolymer in order to provide different color effects for the resulting cast. The invention is also particularly useful in combination with prepolymers other than the water curable polyurethane prepolymers. For example, the casting materials of the invention can be used in combination with two component prepolymer systems, such as epoxy based systems, unsaturated polyester systems and polyurethane systems where the isocyanate is maintained separately from the polyol. In such systems, the casting tape, which is preprinted with a coloring agent, is maintained separately from one or both of the prepolymer reactants until just prior to use. The casting tape may thus be packaged uncoated, or coated with only one component of the system and rolled into a roll. A separate portion of the pouch, or a separate pouch, contains either the second polymer component or the liquid prepolymer. Just prior to using the casting tape to form a cast on the limb of a patient, the physician or cast technician applies the prepolymer material or the second component thereof to the roll in order to initiate hardening of the resin. Various coloring agent printed on fibrous tapes, although not shelf stable for extended periods of time, are stably retained by fibrous tapes in the presence of the liquid prepolymer under these conditions.

The invention has been described in considerable detail with specific reference to various preferred embodiments. However, variations and modifications can be made without departure from the spirit and scope of the invention as described in the foregoing specification and defined in the appended claims.

That which is claimed:

1. An orthopedic cast bandage comprising:
   (a) an open mesh fibrous tape;
   (b) a hardenable liquid resin coated on the fibrous tape and being capable of curing to form a hardened plastic; and
   (c) at least one coloring agent visibly disposed on at least a portion of the fibrous tape, the coloring agent being stably retained by the fibrous tape while the tape is in a soft state in the presence of the hardenable liquid resin, wherein after the liquid resin becomes hard there is substantially no adverse effect on the coloring agent.

2. The orthopedic cast bandage of claim 1 wherein the open mesh fibrous tape comprises fibers selected from the group consisting of polyester, cotton, and glass fibers.

3. The orthopedic cast bandage of claim 2 wherein the hardenable liquid resin is a water hardenable polyurethane prepolymer.

4. The orthopedic cast bandage of claim 3 wherein the liquid resin coated open mesh fibrous tape is storage stable for a period in excess of two months at 50° C. when packaged in a sealed container.

5. The orthopedic cast bandage of claim 1 wherein the liquid resin coated on the fibrous tape is storage stable for a period in excess of one week at 50° C. when packaged in a sealed container.

6. The orthopedic cast bandage of claim 1 wherein the liquid resin coated open mesh fibrous tape has an extensibility of greater than about 10% prior to curing of the liquid resin.

7. The orthopedic cast bandage of claim 1 wherein the open mesh fibrous tape is a knitted polyester fabric comprising textured polyester yarns in the longitudinal direction.

8. The orthopedic cast bandage of claim 1 comprising at least two different coloring agents visibly disposed on at least a portion of the fibrous tape and forming a predetermined visible pattern of at least two colors on the fibrous tape, the coloring agents being stably retained by the fibrous tape in the presence of the hardenable liquid resin.

9. The orthopedic cast bandage of claim 8 wherein the coloring agents visibly disposed on at least a portion of the fibrous tape are pigment printed coloring agents.

10. The orthopedic cast bandage of claim 8 wherein the coloring agents visibly disposed on at least a portion of the fibrous tape are wet printed coloring agents.

11. The orthopedic cast bandage of claim 8 wherein the coloring agents visibly disposed on at least a portion of the fibrous tape are transfer printed coloring agents.

12. The orthopedic cast bandage of claim 1 wherein the coloring agent visibly disposed on at least a portion of the fibrous tape is a pigment printed coloring agent.

13. The orthopedic cast bandage of claim 1 wherein the coloring agent visibly disposed on at least a portion of the fibrous tape is a wet printed coloring agent.

14. The orthopedic cast bandage of claim 1 wherein the coloring agent visibly disposed on at least a portion of the fibrous tape is a transfer printed coloring agent.

15. An orthopedic cast bandage comprising:
    (a) an open mesh fibrous tape;
    (b) a hardenable liquid resin coated on the fibrous tape and being capable of curing to form a hardened plastic; and
    (c) at least one dye penetrated into or chemically bound to at least a portion of the fibrous tape while the tape is in a soft state, the dye being stably retained by the fibrous tape in the presence of the hardenable liquid resin, wherein after the liquid resin becomes hard there is substantially no adverse effect on the dye.

16. The orthopedic cast bandage of claim 15 comprising at least two dyes penetrated into or chemically bound to at least a portion of the fibrous tape and forming a visible, dyed pattern of at least two colors on the fibrous tape.

17. The orthopedic cast bandage of claim 15 wherein the open mesh fibrous tape comprises polyester fibers.

18. The orthopedic cast bandage of claim 17 wherein the open mesh fibrous tape comprises textured polyester yarn in the longitudinal direction.

19. The orthopedic cast tape of claim 15 wherein the open mesh fibrous tape comprises glass fibers.

20. The orthopedic cast tape of claim 15 wherein the liquid resin coated open mesh fibrous tape is storage stable for a period in excess of one week at 50° C. when packaged in a sealed container.

21. The orthopedic cast bandage of claim 15 wherein the dye penetrated into or chemically bound to at least a portion of the fibrous tape comprises a sublimable disperse dye.

22. The orthopedic cast bandage of claim 15 wherein the sublimable disperse dye is disposed on only one side of the open mesh fibrous tape.

23. The orthopedic cast bandage of claim 15 wherein the hardenable liquid resin is a water hardenable polyurethane prepolymer.

24. An orthopedic cast comprising a plurality of layers of open mesh fibrous tape disposed within a hardened polymer matrix, wherein at least the outer layer of the open mesh fibrous tape comprises at least one dye penetrated into or chemically bound to at least a portion of the fibrous tape while the tape is in a soft state, the dye being stably retained by the fibrous tape in the presence of the hardened polymeric matrix, wherein after the hardened polymeric matrix becomes hard there is substantially no adverse effect on the dye.

25. A process for the production of an orthopedic cast bandage comprising the steps:
    (a) contacting an open mesh fibrous tape with a substrate bearing a sublimable dye;
    (b) heating the substrate and the open mesh fibrous tape to cause the sublimable dye to transfer to the open mesh fibrous tape and to thereby color at least a portion of the open mesh fibrous tape; and
    (c) coating the colored, open mesh fibrous tape with a liquid resin capable of curing to form a hardened plastic.

26. The process of claim 25 wherein said open mesh fibrous tape comprises polyester fibers.

27. The process of claim 25 wherein the open mesh fibrous tape comprises glass fibers.

28. The process of claim 25 wherein the open mesh fibrous tape comprises multiple filament textured yarns.

29. The process of claim 25 wherein the substrate bearing a subliminal dye additionally bears at least a second subliminal dye and wherein both of said subliminal dyes are transferred to said open mesh fibrous tape in said heating step.

30. The process of claim 29 wherein said liquid resin capable of curing to form a hardened plastic is a water hardenable polyurethane prepolymer.

31. The process for preparing an orthopedic cast tape comprising the steps:
    (a) providing a knit polyester fabric comprising textured polyester yarn in the longitudinal direction;
    (b) heat treating the knit polyester yarn in a substantially tensionless condition at a first elevated temperature sufficient to cause the knit polyester tape to shrink longitudinally;
    (c) transfer printing the shrunken knit polyester tape in a substantially tension-free state and at a second elevated temperature which is less than or about the same as the first elevated temperature; and
    (d) coating the transfer printed knit tape with a liquid resin capable of curing to form a hardened plastic.

32. The process of claim 31 wherein said transfer printing step is conducted by contacting the shrunken knit polyester tape with a substrate bearing at least two subliminal dyes to thereby transfer both of said subliminal dyes to said shrunken knit polyester tape.

33. The process of claim 32 wherein said liquid resin capable of curing to form a hardened plastic is a water hardenable polyurethane prepolymer.

* * * * *

UNITED STATES PATENT AND TRADEMARK OFFICE
CERTIFICATE OF CORRECTION

PATENT NO. : 5,088,484
DATED : February 18, 1992
INVENTOR(S) : Freeman, et. al.

It is certified that error appears in the above-indentified patent and that said Letters Patent is hereby corrected as shown below:

Column 3, line 19, delete "ion" and insert -- cast of the invention in position --.

Column 4, line 3, delete "30" and substitute -- 12 --.

Signed and Sealed this

First Day of February, 1994

Attest:

BRUCE LEHMAN

*Attesting Officer*  *Commissioner of Patents and Trademarks*

(12) EX PARTE REEXAMINATION CERTIFICATE (6407th)

United States Patent
Freeman et al.

(10) Number: US 5,088,484 C1
(45) Certificate Issued: Sep. 2, 2008

(54) ORTHOPEDIC CASTING BANDAGE

(75) Inventors: Horace L. Freeman, Burlington, NC (US); Hee K. Yoon, North Brunswick, NJ (US)

(73) Assignee: BSN Medical, Inc., Charlotte, NC (US)

Reexamination Request:
No. 90/003,586, Oct. 3, 1994

Reexamination Certificate for:
Patent No.: 5,088,484
Issued: Feb. 18, 1992
Appl. No.: 07/593,852
Filed: Oct. 5, 1990

Certificate of Correction issued Feb. 1, 1994.

(51) Int. Cl.
*A61L 15/00* (2006.01)
*A61L 15/02* (2006.01)
*A61F 5/04* (2006.01)

(52) U.S. Cl. .............................. 602/44; 602/8; 602/900
(58) Field of Classification Search ........................ None
See application file for complete search history.

(56) References Cited

U.S. PATENT DOCUMENTS

| | | | |
|---|---|---|---|
| 3,097,644 | A | 7/1963 | Parker |
| 4,898,159 | A | 2/1990 | Buese et al. |
| 4,968,542 | A | 11/1990 | Gasper et al. |

FOREIGN PATENT DOCUMENTS

| | | |
|---|---|---|
| JP | 63-12768 | 1/1988 |
| ZA | 878838 | 11/1987 |

*Primary Examiner*—Andres Kashnikow (57) ABSTRACT

The invention provides improved orthopedic cast bandages and improved orthopedic casts which include one or more colors. The orthopedic cast bandages of the invention comprise an open mesh fabric tape and a hardenable liquid resin coated onto the fibrous tape. At least one coloring agent is visibly disposed on at least a portion of the fibrous tape. The coloring agent is stably retained by the fibrous tape in the presence of the hardenable liquid resin. Because the coloring agent is stably retained by the fibrous tape, the invention provides for colored orthopedic casting tapes which do not require the use of colored liquid resins. In addition, multiple colored, patterned orthopedic casts, not heretofore available, are provided by the invention.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 24–33 is confirmed.

Claims 1 and 15 are determined to be patentable as amended.

Claims 2–14 and 16–23, dependent on an amended claim, are determined to be patentable.

New claims 34–41 are added and determined to be patentable.

1. An orthopedic cast bandage comprising:
   (a) an open mesh fibrous tape;
   (b) a hardenable liquid resin coated on the fibrous tape and being capable of curing to form a hardened plastic; and
   (c) at least one coloring agent visibly disposed on at least a portion of the fibrous tape *beneath said hardenable liquid resin coating*, the coloring agent being stably retained by the fibrous tape while the tape is in a soft state in the presence of the hardenable liquid resin, wherein after the liquid resin becomes hard there is substantially no adverse effect on the coloring agent.

15. An orthopedic cast bandage comprising:
    (a) an open mesh fibrous tape;
    (b) a hardenable liquid resin coated on the fibrous tape and being capable of curing to form a hardened plastic; and
    (c) at least one dye penetrated into or chemically bound to at least a portion of the fibrous tape *beneath said hardenable liquid resin coating* while the tape is in a soft state, the dye being stably retained by the fibrous tape in the presence of the hardenable liquid resin, wherein after the liquid resin becomes hard there is substantially no adverse effect on the dye.

*34. An orthopedic cast bandage tape comprising:*
   *an open mesh fiberglass tape; an ink printed on said fiberglass tape in a preselected pattern, said ink comprising pigment particles and a bonding resin, said bonding resin being cured and serving to bind said pigment particles to an outer surface of said fiberglass tape; and*
   *a hardenable liquid resin coated on said fiberglass tape and over said preselected pattern of ink, said pigment particles being without any adverse effect from said hardenable liquid resin;*
   *said pigment particles being stably retained by said fiberglass tape while said tape is in a soft state in the presence of said hardenable liquid resin, and there being substantially no adverse effect on said pigment particles after said liquid resin becomes hard.*

*35. The cast bandage tape of claim 34 wherein said open mesh fiberglass tape has extensibility greater than about 15%.*

*36. The cast bandage tape of claim 34 wherein said hardenable liquid resin comprises an isocyanate functional prepolymer.*

*37. The cast bandage tape of claim 34 having a shelf stability greater than two months at 50° C.*

*38. A process of producing an orthopedic cast bandage tape, said process comprising the steps of:*
   *providing an open mesh fiberglass tape;*
   *providing ink comprising pigment particles and a bonding resin;*
   *printing said ink comprising pigment particles and bonding resin as a pattern on said fiberglass tape to form a printed fiberglass tape, said bonding resin being cured and serving to bind said pigment particles to an outer surface of said fiberglass tape; and*
   *applying a hardenable liquid to said fiberglass tape, the pigment particles being without any adverse effect from said hardenable liquid resin;*
   *said pigment particles being stably retained by said fiberglass tape while said tape is in a soft state in the presence of said hardenable liquid resin, and there being substantially no adverse effect on said pigment particles after said liquid resin becomes hard.*

*39. The process of claim 38 wherein said step of printing comprises a pattern of at least two colors.*

*40. The process of claim 38 further comprising the step of heat treatment of the fiberglass tape before said printing step.*

*41. The process of claim 38 wherein said ink particles and bonding resin are in a solvent.*

\* \* \* \* \*